United States Patent
Matsunaga et al.

(10) Patent No.: US 10,786,183 B2
(45) Date of Patent: Sep. 29, 2020

(54) MONITORING ASSISTANCE SYSTEM, CONTROL METHOD THEREOF, AND PROGRAM

(71) Applicant: Omron Corporation, Kyoto (JP)

(72) Inventors: Jumpei Matsunaga, Kyoto (JP); Kiyoaki Tanaka, Kyoto (JP); Shinji Takahashi, Kyoto (JP); Tatsuya Murakami, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 16/461,253

(22) PCT Filed: Nov. 28, 2017

(86) PCT No.: PCT/JP2017/042510
§ 371 (c)(1),
(2) Date: May 15, 2019

(87) PCT Pub. No.: WO2018/159036
PCT Pub. Date: Sep. 7, 2018

(65) Prior Publication Data
US 2019/0313948 A1 Oct. 17, 2019

(30) Foreign Application Priority Data
Mar. 2, 2017 (JP) .................................. 2017-039385

(51) Int. Cl.
*A61B 5/11* (2006.01)
*G08B 21/04* (2006.01)
(Continued)

(52) U.S. Cl.
CPC .......... *A61B 5/1128* (2013.01); *A61B 5/1113* (2013.01); *G08B 21/0476* (2013.01);
(Continued)

(58) Field of Classification Search
None
See application file for complete search history.

(56) References Cited

U.S. PATENT DOCUMENTS

| 4,835,395 A | * | 5/1989 | McManus | ............ | G21C 17/022 250/364 |
| 7,291,118 B2 | * | 11/2007 | McFarland | ............ | A61B 5/103 600/587 |

(Continued)

FOREIGN PATENT DOCUMENTS

| CN | 103118588 A | 5/2013 |
| CN | 104361321 A | 2/2015 |

(Continued)

OTHER PUBLICATIONS

International Search Report issued in Application No. PCT/JP2017/042510, dated Feb. 20, 2018 (1 page).

(Continued)

*Primary Examiner* — Fekadeselassie Girma
(74) *Attorney, Agent, or Firm* — Osha Liang LLP (57) ABSTRACT

A watching assistance system that assists watching over a subject on a bed includes an image acquisition unit configured to acquire an image captured by an imaging device, a criterion storage in which a criterion for determining a dangerous state are previously set for each of a plurality of determination regions set based on a region of the bed in the image, a detector configured to detect the subject from the image acquired by the image acquisition unit, a state recognition unit configured to recognize a state of the subject detected by the detector, a determination unit configured to determine a danger degree of the state of the subject recognized by the state recognition unit using the criterion for the determination region corresponding to a position at which the subject is detected by the detector, and an output unit (Continued)

configured to provide notification according to the danger degree determined by the determination unit.

7 Claims, 11 Drawing Sheets

(51) Int. Cl.
  *A61B 5/00*    (2006.01)
  *G06K 9/00*    (2006.01)
  *H04N 7/18*    (2006.01)

(52) U.S. Cl.
  CPC ............ *A61B 5/1117* (2013.01); *A61B 5/746* (2013.01); *G06K 9/00771* (2013.01); *G08B 21/043* (2013.01); *H04N 7/188* (2013.01); *H04N 2201/0079* (2013.01)

(56) References Cited

U.S. PATENT DOCUMENTS

| | | | |
|---|---|---|---|
| 9,492,341 B2* | 11/2016 | Huster | A61B 5/1115 |
| 10,482,321 B2* | 11/2019 | Kusens | G06K 9/00771 |
| 2006/0021615 A1* | 2/2006 | Kertzman | A61M 16/1045 |
| | | | 128/201.13 |
| 2006/0049936 A1* | 3/2006 | Collins, Jr. | G16H 40/20 |
| | | | 340/539.11 |
| 2007/0143920 A1* | 6/2007 | Frondorf | A61G 7/0513 |
| | | | 5/81.1 R |
| 2008/0212828 A1* | 9/2008 | Ishida | G06K 9/00288 |
| | | | 382/100 |
| 2008/0231461 A1* | 9/2008 | Sanchez | G08B 21/06 |
| | | | 340/575 |
| 2009/0062622 A1* | 3/2009 | Lin | A47D 9/02 |
| | | | 600/300 |
| 2012/0029879 A1* | 2/2012 | Sing | A61B 5/1121 |
| | | | 702/189 |
| 2012/0046009 A1* | 2/2012 | Persson | H04M 1/05 |
| | | | 455/404.2 |
| 2012/0075464 A1* | 3/2012 | Derenne | A61B 5/1113 |
| | | | 348/135 |
| 2012/0242819 A1* | 9/2012 | Schamp | A61B 5/18 |
| | | | 348/78 |
| 2013/0182092 A1 | 7/2013 | Ishii et al. | |
| 2014/0000033 A1* | 1/2014 | Clenet | A61G 7/015 |
| | | | 5/618 |
| 2014/0036647 A1 | 2/2014 | Yoshizawa et al. | |
| 2014/0104404 A1* | 4/2014 | Locke | G08B 21/02 |
| | | | 348/77 |
| 2014/0267663 A1* | 9/2014 | Yasukawa | G06K 9/00771 |
| | | | 348/77 |
| 2014/0320290 A1* | 10/2014 | Reeder | A61B 5/1113 |
| | | | 340/573.1 |
| 2015/0109442 A1* | 4/2015 | Derenne | A61B 5/1113 |
| | | | 348/143 |
| 2015/0136146 A1* | 5/2015 | Hood | A61B 5/6892 |
| | | | 128/845 |
| 2015/0164721 A1* | 6/2015 | Miyashita | A61G 7/015 |
| | | | 5/617 |
| 2015/0335507 A1* | 11/2015 | Emmons | G16H 50/30 |
| | | | 5/615 |
| 2016/0008197 A1* | 1/2016 | Zerhusen | A61G 7/0513 |
| | | | 5/503.1 |
| 2016/0140827 A1* | 5/2016 | Derenne | A61B 5/747 |
| | | | 340/573.7 |
| 2016/0143796 A1* | 5/2016 | Jordan | A61G 7/08 |
| | | | 701/70 |
| 2016/0192886 A1* | 7/2016 | Nunn | A47C 27/083 |
| | | | 700/282 |
| 2016/0307429 A1* | 10/2016 | Hood | A61G 7/018 |
| 2016/0314672 A1* | 10/2016 | Wiggermann | A61B 5/1071 |
| 2017/0053190 A1* | 2/2017 | Cheatham | G06K 9/00362 |
| 2017/0053401 A1 | 2/2017 | Hata et al. | |
| 2017/0076148 A1* | 3/2017 | Sashida | G06K 9/00248 |
| 2018/0000407 A1* | 1/2018 | Johnson | G01S 13/58 |
| 2018/0035082 A1* | 2/2018 | Patil | A61B 5/746 |
| 2018/0110667 A1* | 4/2018 | Freeman | A61G 13/08 |
| 2018/0174320 A1 | 6/2018 | Hayashi et al. | |
| 2018/0214091 A1* | 8/2018 | Baker | G16H 40/63 |
| 2020/0008734 A1* | 1/2020 | Bhandari | A61M 21/00 |

FOREIGN PATENT DOCUMENTS

| | | |
|---|---|---|
| CN | 106413545 A | 2/2017 |
| JP | 2012-71004 A | 4/2012 |
| JP | 2012-170483 A | 9/2012 |
| JP | 2017/042510 | 2/2018 |
| WO | 2016143641 A1 | 9/2016 |

OTHER PUBLICATIONS

Written Opinion issued in International Application No. PCT/JP2017/042510, dated Feb. 20, 2018 (8 pages).
Office Action issued in Chinese Application No. 201780070868.0; dated Jul. 10, 2020 (16 pages).

* cited by examiner

MONITORING ASSISTANCE SYSTEM, CONTROL METHOD THEREOF, AND PROGRAM

TECHNICAL FIELD

The present invention relates to a technique of assisting watching over a subject on a bed.

BACKGROUND ART

In order to prevent a fall accident from a bed, there is a system that assists watching over a patient in a hospital or a nursing facility. Patent Document 1 proposes a system that recognizes motion of the patient (moving a head/trying to raise up/raised/turning over/trying to get down/got down) from a camera image, and provides notification at an appropriate alarm level depending on a combination of an action content of the patient and a condition (bad/ordinary/good) of the patient. Patent Document 2 proposes a system that detects a moving direction of the patient from the camera image, and determines a current state of the patient based on the combination of the moving direction of the patient and the past state (going-to-bed state/raising-up state/getting-out-of-bed state/absent state).

PRIOR ART DOCUMENTS

Patent Documents

Patent Document 1: Japanese Unexamined Patent Publication No. 2012-071004
Patent Document 2: Japanese Unexamined Patent Publication No. 2012-170483

SUMMARY OF THE INVENTION

Problems to be Solved by the Invention

As described above, the attempt to detect the motion or state of a person from the camera image to use the motion or state for watching assistance has conventionally been made. However, although the getting-out-of-bed state of the patient can be detected, safely getting out of bed or a possibility of a tumble or a fall cannot be distinguished from each other. Whether the current state of the patient is safe or dangerous cannot be determined. Thus, in the conventional method, there is a problem in that the alarm is sounded despite the safety state of the patient to trouble a nurse or the like.

The present invention has been made in view of the above-mentioned circumstances, and an object of the present invention is to provide a technology capable of quickly and accurately detecting a dangerous state of the subject on the bed.

Means for Solving the Problem

In order to achieve the above object, the present invention adopts a method for setting a plurality of determination regions based on the region of the bed and switching the criterion of a danger degree in each determination region.

According to a first aspect of the present invention, a watching assistance system that assists watching over a subject on a bed, the watching assistance system includes: an image acquisition unit configured to acquire an image captured by an imaging device; a criterion storage in which a criterion for determining a dangerous state are previously set for each of a plurality of determination regions set based on a region of the bed in the image; a detector configured to detect the subject from the image acquired by the image acquisition unit; a state recognition unit configured to recognize a state of the subject detected by the detector; a determination unit configured to determine a danger degree of the state of the subject recognized by the state recognition unit using the criterion for the determination region corresponding to a position at which the subject is detected by the detector; and an output unit configured to provide notification according to the danger degree determined by the determination unit.

With this configuration, whether the subject is in the safe state or the dangerous state can be determined from the image. In particular, a plurality of determination regions are set based on the region of the bed, and the criterion is switched according to the position at which the subject is detected, so that the danger of the subject on the bed is detected more quickly and more accurately than in the past. The notification is provided according to the danger degree, so that convenience for a person receiving the notification can be improved.

In the present invention, preferably the state recognition unit recognizes the state of the head of the subject, and the determination unit determines the danger degree of the state of the head. The dangerous behavior of the subject can accurately be detected by monitoring the state of the head. Specifically, preferably the state of the head includes at least one item of a head orientation, a head moving speed, a head moving direction, and a head moving vector.

Preferably the state of the head includes a plurality of items of a head orientation, a head moving speed, a head moving direction, and a head moving vector, and the determination unit determines the danger degrees relating to the plurality of items. The danger degree can be determined with higher reliability by comprehensively evaluating the state of the subject using the danger degree relating to the plurality of items.

Preferably the output unit does not provide notification when the determined danger degree is smaller than a threshold. The necessary notification is provided only in the case it is necessary according to the danger degree, so that the problem that the alarm is sounded despite the safe state of the subject to trouble a nurse or the like can be solved.

The present invention can be recognized as a watching assistance system having at least a part of the above configuration and function. The present invention can also be recognized as a watching assistance method or a watching assistance system control method including at least a part of the above processing, a program causing a computer to perform these methods, or a computer-readable recording medium in which the program is non-transiently recorded. The above configurations and processes can be combined with each other as long as a technical contradiction is not generated.

Effect of the Invention

In the present invention, the dangerous state of the subject on the bed can quickly and accurately be detected.

MODE FOR CARRYING OUT THE INVENTION

The present invention relates to a technique of assisting watching over a subject on a bed. The technique can be applied to a system that automatically detects getting-out-of-bed and rising behaviors of the patients or those dependent on care in a hospital or nursing facility, and provides necessary notification when a dangerous state is generated. For example, the system can preferably be used to assist watching over elderly people, patients with dementia, and children.

Hereinafter, an example of a preferred aspect for carrying out the present invention will be described with reference to the drawings. However, a configurations and an operation of a device described in the following embodiment are merely examples, and the scope of the present invention is not limited thereto.

(System Configuration)

Figure 1:
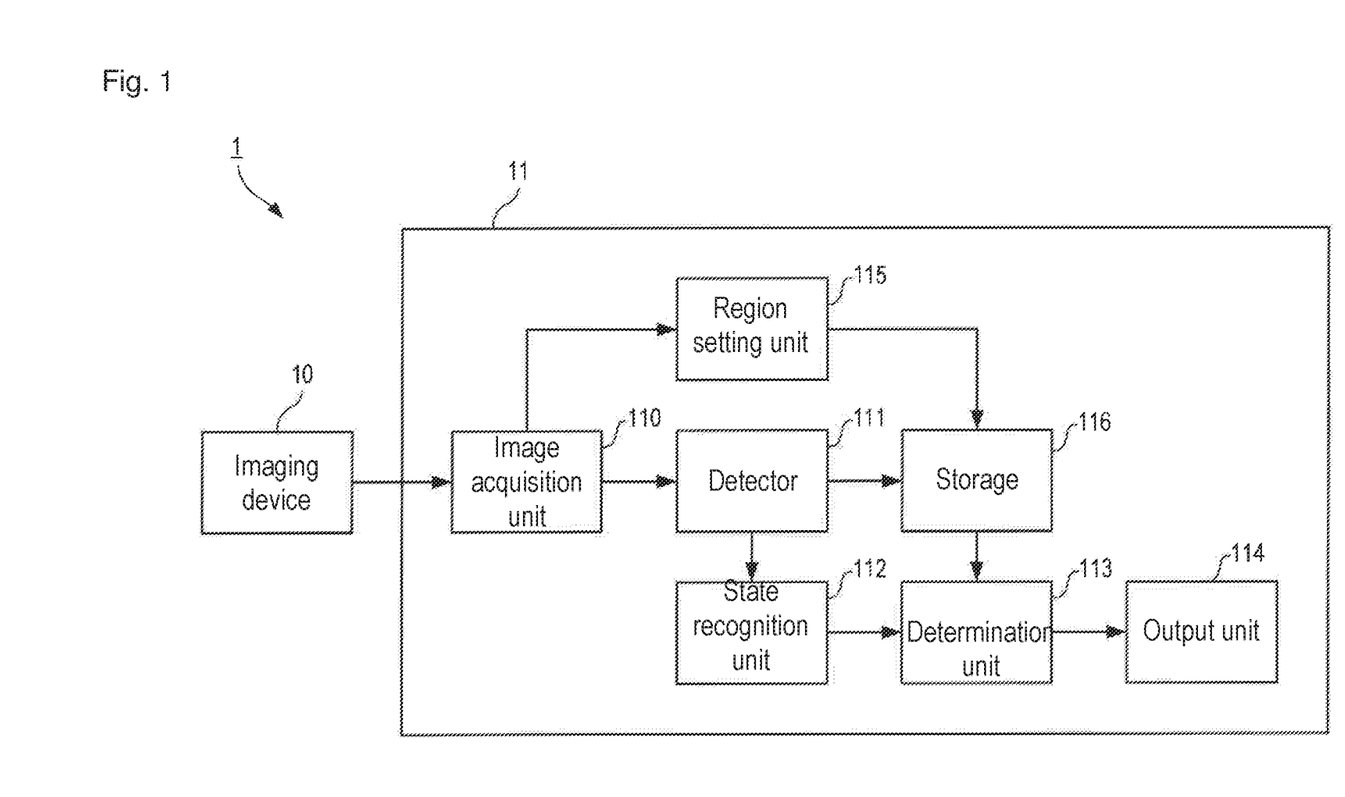
FIG. 1 is a block diagram schematically illustrating a hardware configuration and a functional configuration of a watching assistance system.
Figure 2:
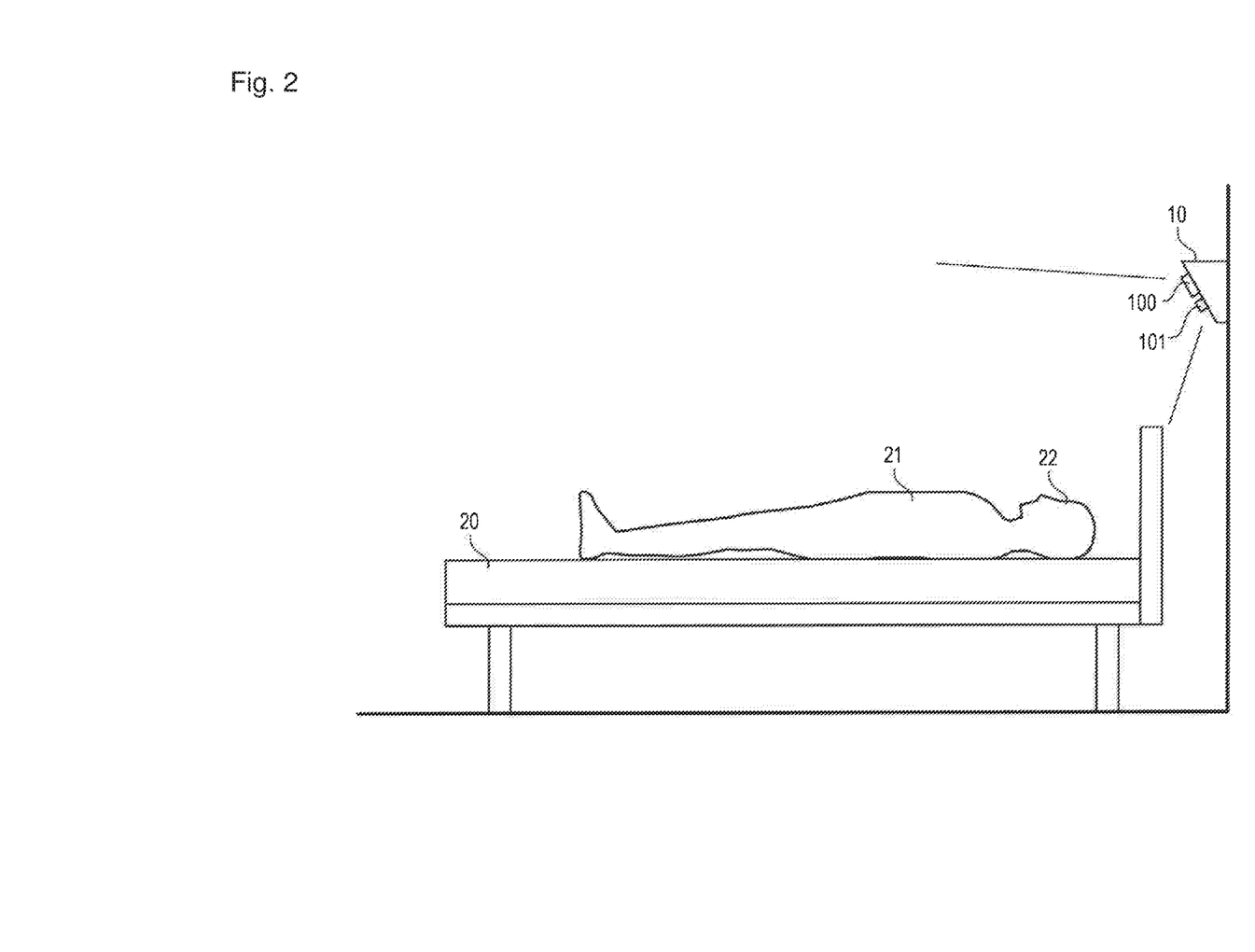
FIG. 2 is a view illustrating an installation example of an imaging device.

The configuration of a watching assistance system according to an embodiment of the present invention will be described with reference to FIGS. 1 and 2. FIG. 1 is a block diagram schematically illustrating a hardware configuration and a functional configuration of a watching assistance system 1, and FIG. 2 is a view illustrating an installation example of an imaging device.

The watching assistance system 1 includes an imaging device 10 and an information processing device 11 as a main hardware configuration. The imaging device 10 and the information processing device 11 are connected to each other in a wired or wireless manner. Although only one imaging device 10 is illustrated in FIG. 1, a plurality of imaging devices 10 may be connected to the information processing device 11.

The imaging device 10 is a device that images the subject on the bed to capture image data. A monochrome or color visible light camera, an infrared camera, and the like can be used as the imaging device 10. In the embodiment, the imaging device 10 constructed with an infrared LED illumination 100 and a near infrared camera 101 is used in order to enable the watching over the subject even at night (even when a room is dark). As illustrated in FIG. 2, the imaging device 10 is installed to look over an entire bed 20 from an upper side of a head side of a bed 20 toward a foot side. The imaging device 10 captures an image at predetermined time intervals (for example, 10 fps), and the image data is sequentially captured by the information processing device 11.

The information processing device 11 is a device having a function of analyzing the image data captured from the imaging device 10 in real time, and automatically detecting whether a subject 21 on the bed 20 is abnormal (is not in a dangerous state). The information processing device 11 includes an image acquisition unit 110, a detector 111, a state recognition unit 112, a determination unit 113, an output unit 114, a region setting unit 115, and a storage 116 as a specific function. The information processing device 11 of the embodiment includes a CPU (processor), a memory, a storage (such as an HDD and an SSD), an input device (such as a keyboard, a mouse, and a touch panel), an output device (such as a display and a speaker), and a communication interface. The CPU executes a program stored in the storage or the memory to implement each function of the information processing device 11. However, the configuration of the information processing device 11 is not limited to this example. For example, distributed computing may be performed by a plurality of computers, a part of the above functions may be performed by a cloud server, or a part of the above functions may be performed by a circuit such as an ASIC or an FPGA.

The image acquisition unit 110 is a function of acquiring the image captured by the imaging device 10. The image data input from the image acquisition unit 110 is temporarily stored in a memory or a storage, and used in processing of the detector 111 and the state recognition unit 112.

The detector 111 is a function of analyzing the image acquired by the image acquisition unit 110 to detect a human body of the watching subject 21 or a part (such as a head, a face, and an upper body) of the human body from the image. Any method may be adopted as a method for detecting the human body or the part of the human body from the image. For example, an object detection algorithm using a technique based on a discriminator in which a classic Haar-like feature quantity or HoG feature quantity is used or a technique in which recent Faster R-CNN is used can preferably be used. The detector 111 of the embodiment detects a head (a part above a neck) 22 of the subject 21 by the discriminator in which the Haar-like feature quantity is used, and outputs a position (x, y) and a size (the numbers of vertical and horizontal pixels) of the head 22 as a detection result. For example, the position (x, y) of the head 22 is represented by an image coordinate of a center point of a rectangular frame surrounding the head 22. The detector 111 of the embodiment outputs the detection result in terms of the position and size of an image coordinate system. Alternatively, the detector 111 may convert the image coordinate system into a spatial coordinate system, and output a three-dimensional position or a three-dimensional size in the spatial coordinate system of the subject 21.

The state recognition unit 112 has a function of recognizing the state of the subject 21 detected by the detector 111. In the embodiment, the state of the head 22 of the subject 21, specifically, at least one of (1) orientation of the head 22, (2) a moving speed of the head 22, and (3) a moving direction of the head 22 is calculated.

For example, the orientation of the head 22 may be recognized based on a positional relationship of facial organs (such as eyes, a nose, and a mouth) in the image of the head 22, or recognized using a plurality of kinds of discriminators that learn in each orientation of the head 22 or another algorithm. As to the orientation of the head 22, a continuous value (angle) may be calculated, and which one of previously-determined N types of orientations (directions) such as a right direction, a front orientation, and a left orientation corresponds to may be determined. The orientations around three axes of yaw, pitch, and roll may be calculated, or the orientations in the image coordinate system (in an xy plane) may simply be calculated.

The moving speed of the head 22 is a moving amount of the head 22 per predetermined time. For example, the moving speed can be obtained by calculating a distance between the position of the head 22 in the image of a plurality of frames earlier and the position of the head 22 in the latest image. For example, the moving direction of the head 22 can be calculated from the orientation (angle) of a line connecting the position of the head 22 in the image of a plurality of frames earlier and the position of the head 22 in the latest image. The movement speed and the moving direction may be combined to obtain a movement vector of the head 22. In this case, the moving speed, the moving direction, and the moving vector in a real space (three-dimensional space) may be calculated by converting the image coordinate system into the spatial coordinate system.

The determination unit 113 is a function of determining whether the subject 21 is in a safe state or a dangerous state based on results of the detector 111 and the state recognition unit 112. Specifically, using the "criterion" for evaluating and determining the dangerous state, the determination unit 113 performs processing of determining a danger degree of the state (at least one of the orientation, the moving speed, the moving direction, and the moving vector) of the head 22 recognized by the state recognition unit 112. The danger degree may be determined by a two-step determination of safety and danger, or determined by a multi-step determination such as the danger degree=0, 1, 2, . . . . In the feature of the embodiment, a plurality of criteria are previously set in a criterion storage of the storage 116, and the determination unit 113 switches the criterion to be used according to the position at which (the head 22 of) the subject 21 is detected. This feature will be described in detail later.

The output unit 114 is a function of providing notification according to a danger degree determined by the determination unit 113. The output unit 114 switches necessity (for example, provides notification only in the case of the dangerous state) of the notification, a notification content (for example, a content of a message), notification means (for example, a voice, a mail, a buzzer, or a warning light), a notification destination (for example, a nurse or a doctor), a notification frequency, and the like according to the danger degree.

The region setting unit 115 is a function of setting a determination region to the image captured by the imaging device 10. In order to monitor the state of the subject 21 on the bed 20, the watching assistance system 1 sets the determination region based on the region of the bed 20 in the image. The setting of the determination region may manually or automatically be performed. For the manual setting, the region setting unit 115 may provide a user interface that allowing a user to input a bed region or the determination region in the image. For the automatic setting, the region setting unit 115 may detect the bed region from the image by object recognition processing.

The storage 116 is a function of storing various data used in the processing by the watching assistance system 1. A storage area is provided in the storage 116 in order to store at least setting information about a criterion, setting information about the determination region, image data of a plurality of past frames, or detection results (used to calculate of the moving speed or the moving direction).

(Setting of Determination Region)

Figure 3:
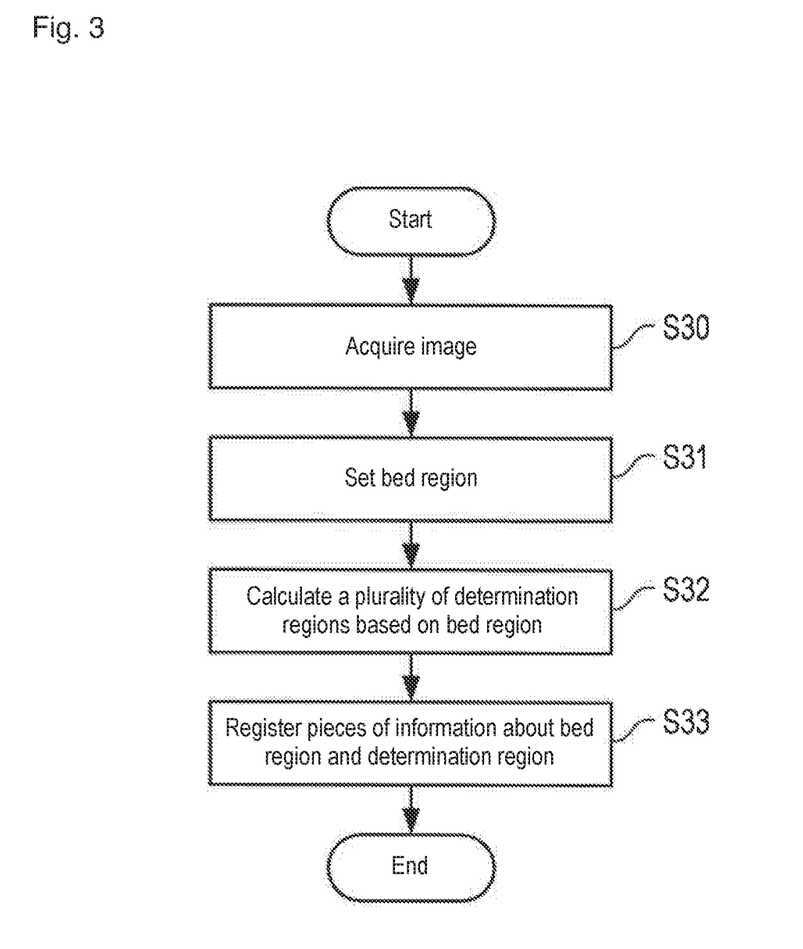
FIG. 3 is a flowchart illustrating processing of setting a determination region.
Figure 4:
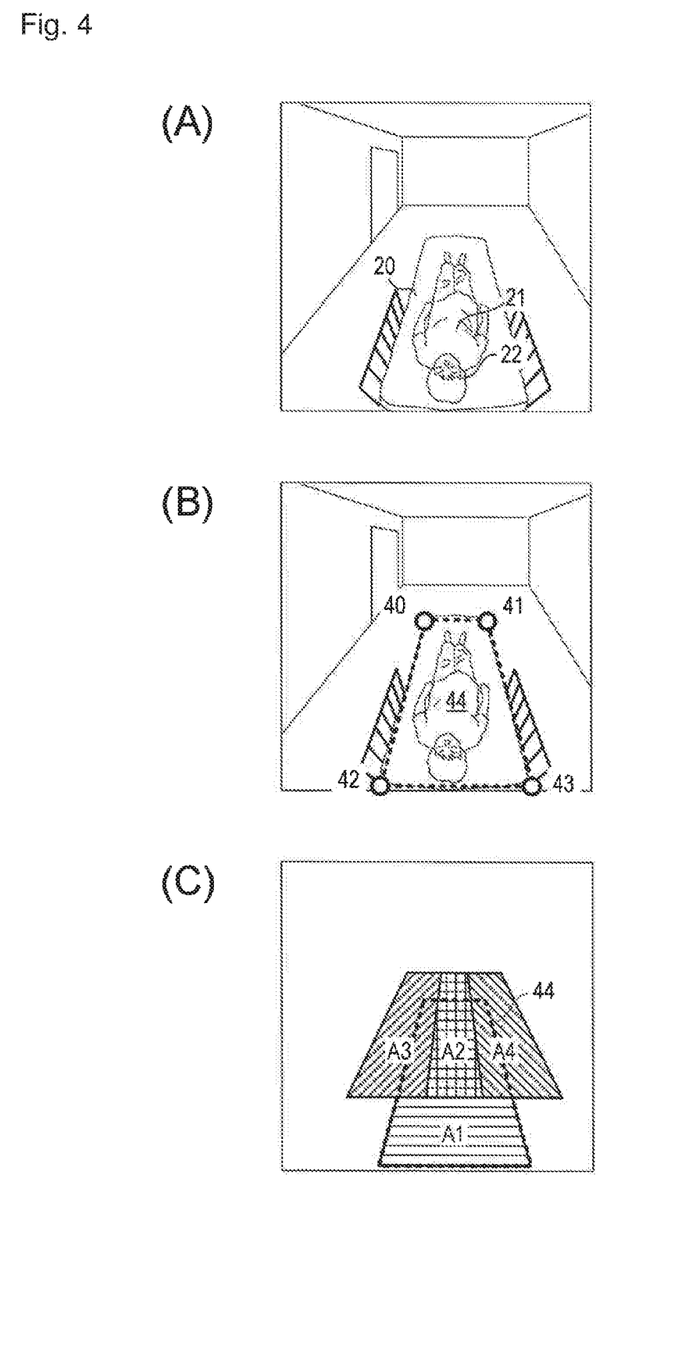
FIGS. 4A to 4C illustrate examples of the determination region set to an image.

An example of determination region setting processing will be described with reference to FIGS. 3, 4A to 4C. FIG. 3 is a flowchart of the determination region setting processing performed by the information processing device 11, and FIGS. 4A to 4C illustrate examples of the determination region set to the image. The determination region setting processing is performed when the determination region is not set (for example, at time of installation of the watching assistance system 1) or when the determination region needs to be updated with the movement of the bed or the imaging device 10.

In step S30, the image acquisition unit 110 acquires the image from the imaging device 10 (FIG. 4A). In step S31, the region setting unit 115 causes the user to input points 40 to 43 at the four corners of the bed, and sets a quadrangle surrounded by the four points 40 to 43 in a bed region 44 (FIG. 4B). In step S32, the region setting unit 115 calculates a range of four determination regions A1 to A4 based on the bed region 44 (FIG. 4C). In step S33, the region setting unit 115 stores information about the bed region 44 (coordinates of the four corners of the bed region 44) and information about the four determination regions A1 to A4 (coordinates of the four corners of each determination region) in storage unit 116. Then, the setting processing is ended.

The determination region A1 is a region set onto the head side of the bed 20, and corresponds to a range where the head 22 may exist in the case that the subject 21 sleeps in the bed 20. The determination region A2 is a region set to the center of the foot side of the bed 20, and corresponds to the range where the head 22 may exist in the case that the subject 21 raises an upper body from the state in which the subject 21 is lying or in the case that the subject 21 gets down or falls from the foot side of the bed 20. The determination region A3 is a region set to the left of the foot side of the bed 20, and corresponds to the range where the head 22 may exist in the case that the subject 21 is seated on a left edge of the bed 20 or in the case that the subject 21 descends or falls from the left of the bed 20. The determination region A4 is a region set to the right of the foot side of the bed 20, and corresponds to the range where the head 22 may exist in the case that the subject 21 is seated on a right edge of the bed 20 or in the case that the subject 21 descends or falls from the right of the bed 20. As illustrated in FIG. 4C, the determination regions A2 to A4 extend to the outside of the bed region 44.

The reason the plurality of determination regions are set in this way is that the evaluation of the safe state or the dangerous state may change depending on where the subject 21 exists on the bed 20. For example, in the case that the head 22 of the subject 21 exists in the determination region A1, it is considered that the subject 21 is lying on the bed 20 in a normal posture, and the head 22 has largely moved or changed its orientation. Also, a risk that the subject 21 falls from the bed 20 is low even if the head 22 moves largely or the orientation of the head 22 changes largely. In the case that the head 22 of the subject 21 exists in the determination region A3, when the head 22 is oriented toward the left, it is considered that the subject 21 gets off from the bed 20 with its own intention, and the danger degree can be evaluated to be low. On the other hand, when the head 22 is oriented toward the upper, lower, or right side, it should be determined that some sort of abnormality or a falling risk is generated. The determination region A4 is determined opposite to the left and right of the determination region A3.

Figure 5:
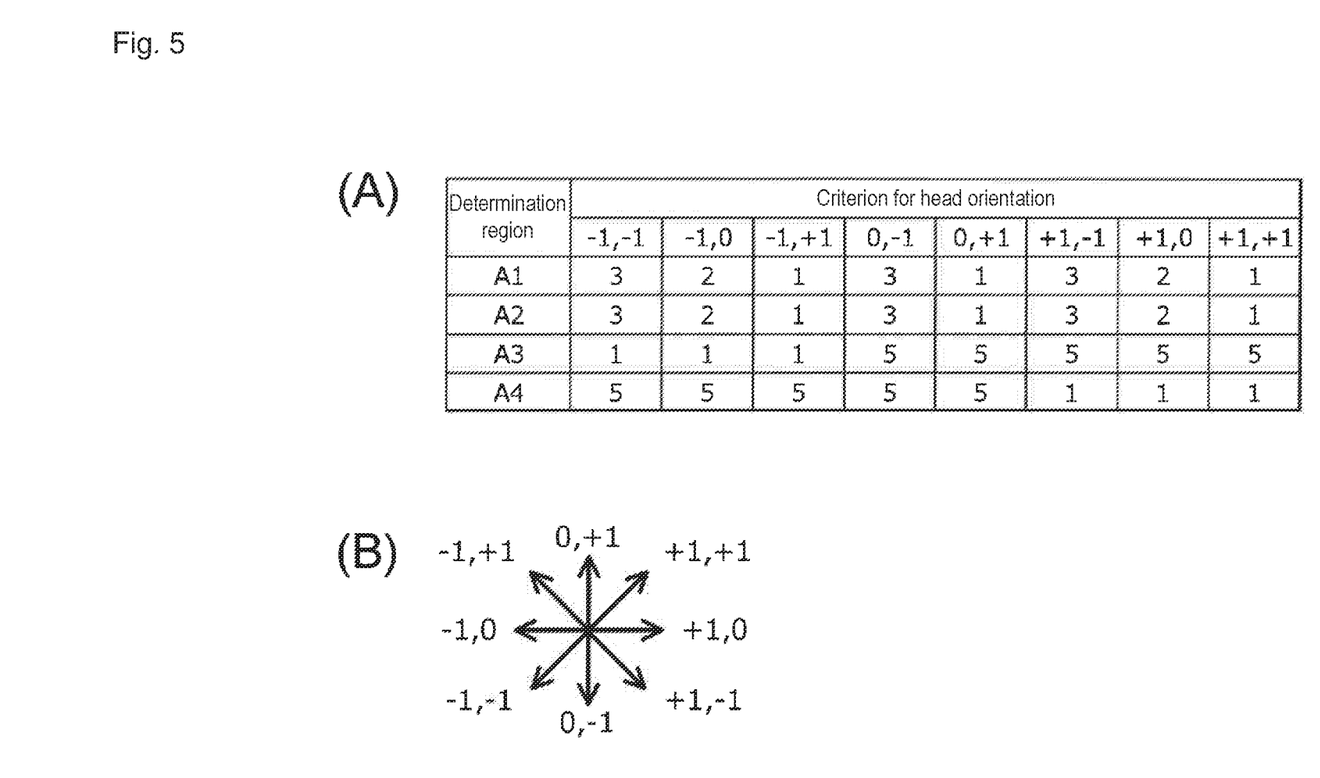
FIG. 5A illustrates an example of a data structure of a criterion of head orientation in each determination region.
FIG. 5B is a diagram illustrating codes representing eight directions.

FIG. 5A illustrates an example of a data structure of the criterion set in the storage 116. FIG. 5A illustrates an example of the criterion for the head orientation. The symbols such as "−1,−1", "−1,0", . . . indicate the head orientation (eight directions) as illustrated in FIG. 5B, and a value of the criterion indicates the danger degree. The higher the danger degree indicates higher with increasing value, the value of 1 is the head orientation with the lowest danger degree, and the value of 5 is the head orientation with the highest danger degree. As described above, because the evaluation of the safe state or the dangerous state changes in each of the determination regions A1 to A4, the criterion storage of the storage 116 is correlated with a different criterion in each determination region. Although the example in FIG. 5A is the criterion for the head orientation, criteria corresponding to a plurality of items, such as the moving speed and the moving direction of the head, which are used in the evaluation by the determination unit 113, may be set.

A specific example of the watching processing performed by the watching assistance system 1 of the embodiment will be described below.

Example 1

Figure 6:
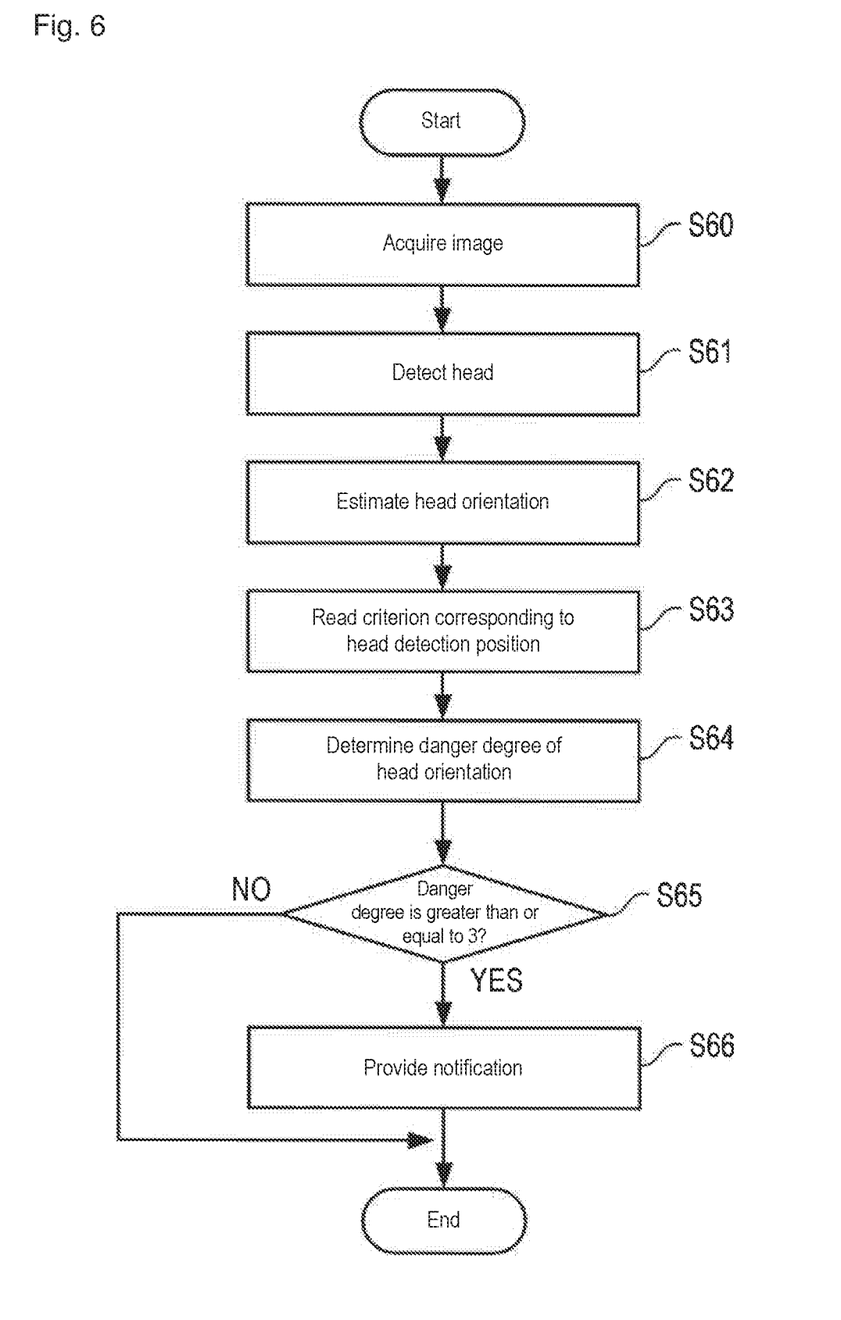
FIG. 6 is a flowchart illustrating watching processing of Example 1.
Figure 7:
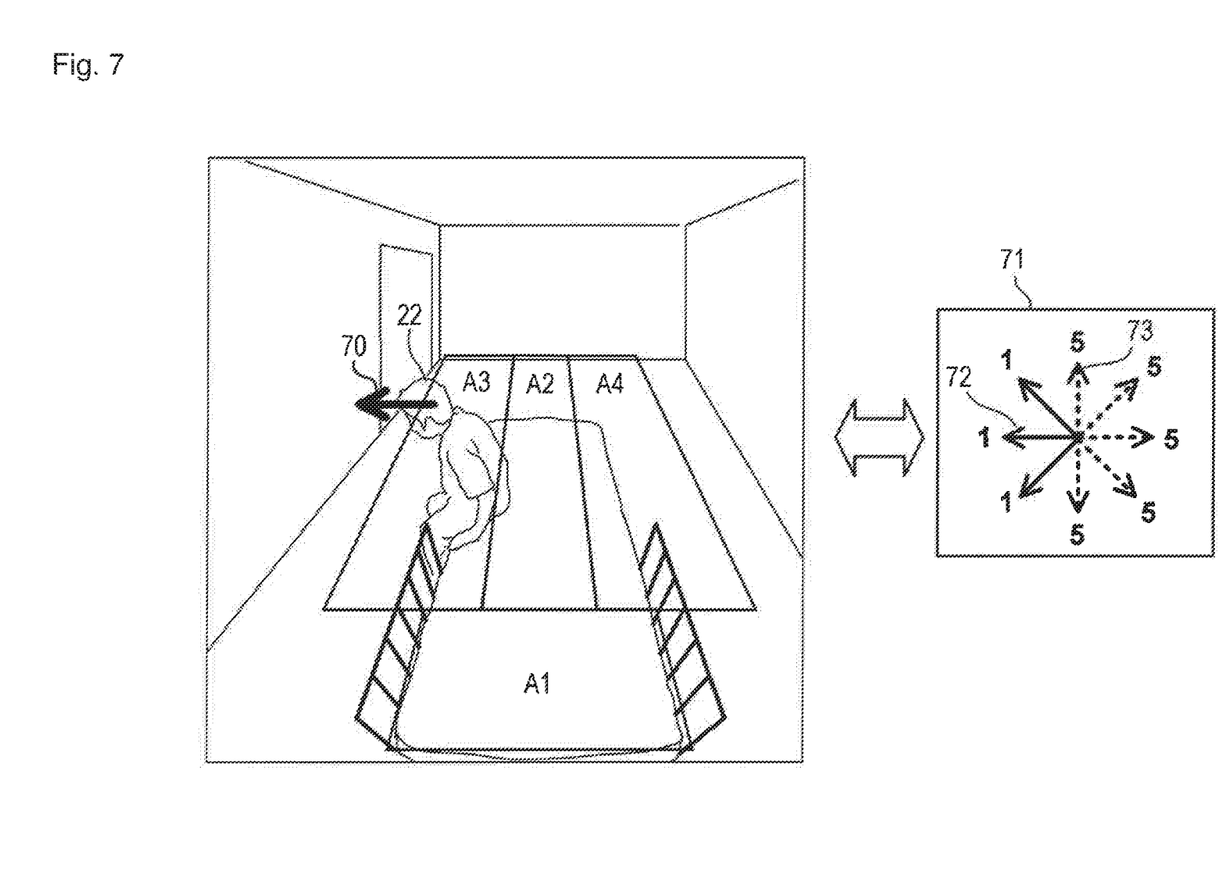
FIG. 7 illustrates an example of a danger degree determination of Example 1.

An example of the watching processing of Example 1 will be described with reference to FIGS. 6 and 7. FIG. 6 is a flowchart of the watching processing of Example 1 performed by the information processing device 11, and FIG. 7 is an example of the danger degree determination.

In step S60, the image acquisition unit 110 acquires the image from the imaging device 10. The acquired image is temporarily stored in the storage 116. In step S61, the detector 111 detects the subject head from the image acquired in step S60. In step S62, the state recognition unit 112 estimates the orientation of the head detected in step S61. FIG. 7 illustrates an example in which the head 22 is detected in the determination region A3 and the orientation of the head 22 is estimated to be the direction of an arrow 70.

In step S63, the determination unit 113 reads the criterion corresponding to the determination region A3 from the storage 116. The symbol 71 in FIG. 7 schematically illustrates the criterion corresponding to the determination region A3, a solid arrow 72 indicates "safe orientation" (danger degree=1), and a broken arrow 73 indicates "dangerous orientation" (danger degree=5). In step S64, the determination unit 113 determines whether the orientation (arrow 70) of the head 22 is the safe orientation or the dangerous orientation using the criterion corresponding to the determination region A3. In the example of FIG. 7, the determination result of the safe orientation (danger degree=1) is obtained. That is, because the head 22 is oriented toward the outside of the bed, it is considered that the subject gets off from the bed by its own intention, and the danger degree is determined to be low.

Subsequently, the output unit 114 provides notification according to the danger degree (step S65). In Example 1, the notification (for example, a nurse call) is provided when the danger degree is greater than or equal to a predetermined threshold (for example, 3) (step S66), and the notification is not provided when the danger degree is smaller than the threshold. Thus, the notification is not provided in the case of the example in FIG. 7.

According to the method described above, whether the subject is in the safe state or the dangerous state can be determined from the image, so that the danger of the subject on the bed can be detected more quickly and more accurately than in the past. The necessary notification is provided only in the case it is necessary according to the danger degree, so that the problem that the alarm is sounded despite the safe state of the subject to trouble a nurse or the like can be solved.

Example 2

Figure 8:
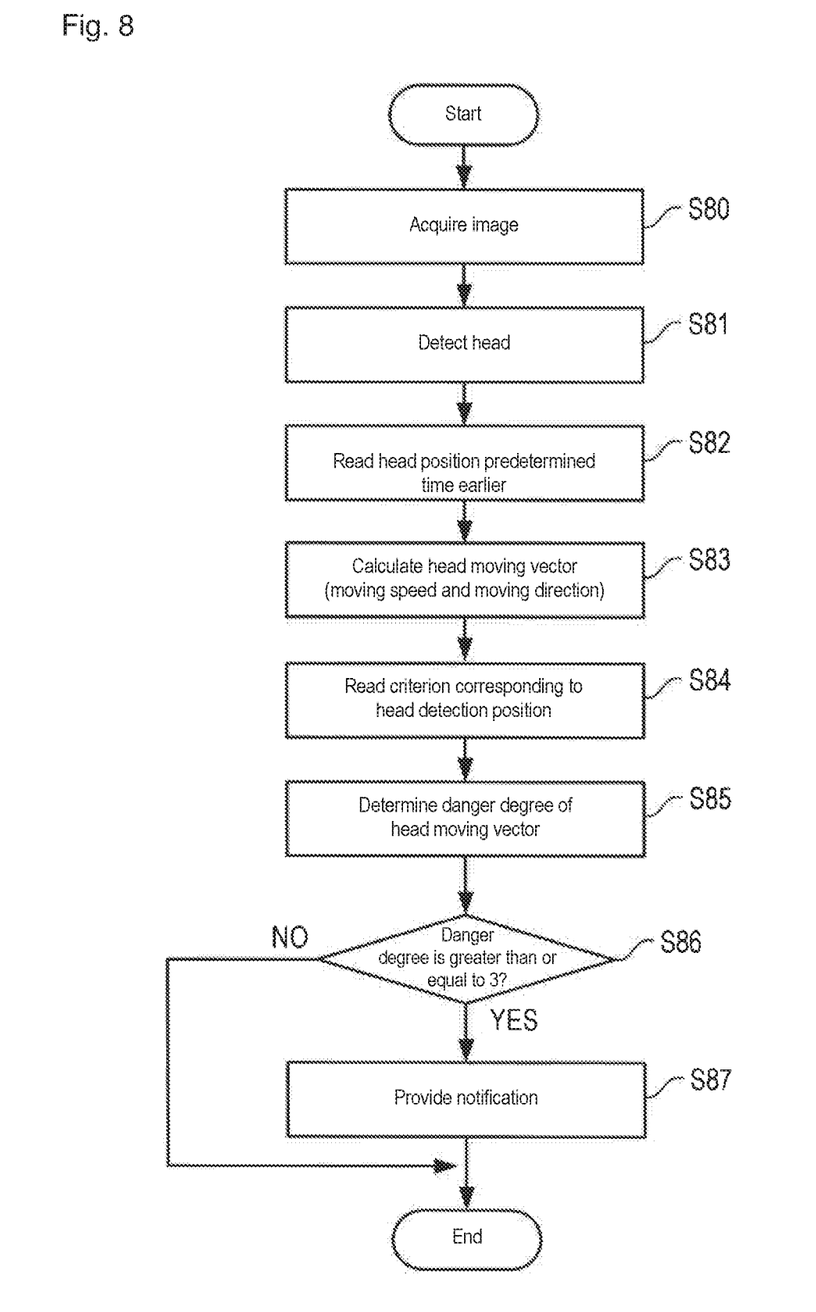
FIG. 8 is a flowchart illustrating watching processing of Example 2.
Figure 9:
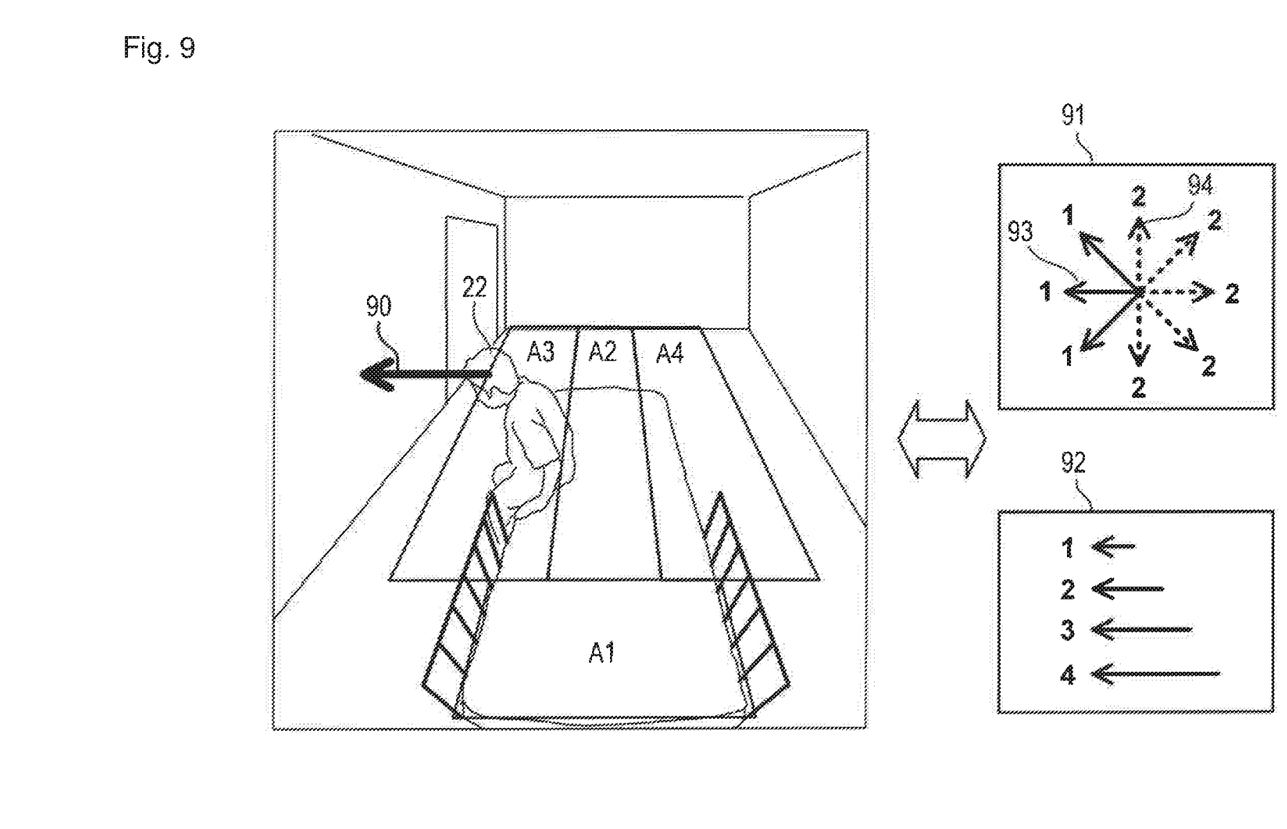
FIG. 9 illustrates an example of a danger degree determination of Example 2.

An example of the watching processing of Example 2 will be described with reference to FIGS. 8 and 9. FIG. 8 is a flowchart of the watching processing of Example 2 performed by the information processing device 11, and FIG. 9 is an example of the danger degree determination.

In step S80, the image acquisition unit 110 acquires the image from the imaging device 10. The acquired image is temporarily stored in the storage 116. In step S81, the detector 111 detects the subject head from the image acquired in step S80. The information about the detected head position is stored in the storage 116 while correlated with time information or a frame number of the image. The state recognition unit 112 reads the information about the head position in the image of a predetermined time earlier (for example, one second) from the storage 116 (step S82). Based on the head position of the predetermined time earlier and the head position detected in step S81, the moving speed (moving amount per predetermined time) and the moving direction of the head are calculated to obtain the moving vector of the head (step S83). FIG. 9 illustrates an example in which the head 22 is detected in the determination region A3 and the moving vector of the head 22 is calculated as indicated by an arrow 90.

In step S84, the determination unit 113 reads the criterion corresponding to the determination region A3 from the storage 116. The symbols 91, 92 in FIG. 9 schematically illustrate the criterion corresponding to the determination region A3. The symbol 91 is an example of the criterion relating to the moving direction, and a solid arrow 93 indicates the "safe direction" (danger degree=1), and a broken arrow 94 indicates the "dangerous direction" (danger degree=2). The symbol 92 is an example of the criterion relating to the moving speed (moving amount), and indicates that the danger degree increases with increasing length of the arrow. In this example, four levels of danger degree of 1 to 4 are assigned according to the moving speed.

In step S85, the determination unit 113 determines the danger degree of the moving vector 90 of the head 22 using the criteria 91, 92. For example, a product (multiplication value) or a sum (addition value) of the danger degree in the moving direction and the danger degree in the moving speed can be used as the danger degree of the moving vector 90. In the example of FIG. 9, the moving speed is large (danger degree=4) although the moving direction is safe (danger degree=1), so that the determination result that the moving vector 90 has the danger degree of 4 (in the case of the multiplication value) is obtained. That is, although the moving direction of the subject 21 is the direction in which the subject 21 gets down from the bed when only the moving direction of the head 22 is viewed, the moving speed (moving amount) of the head 22 is very high, so that the action is regarded as not normal action to get off from the bed but the motion to tumble or fall from the bed, and the danger degree is determined to be high.

Subsequently, the output unit 114 provides the notification according to the danger degree (step S86). In Example 2, the notification (for example, a nurse call) is provided in the case that the danger degree is greater than or equal to a predetermined threshold (for example, 3) (step S87). Thus, the notification is provided in the case of the example in FIG.

9. Similarly to Example 1, by the method of Example 2, the danger of the subject on the bed can be detected more quickly and more accurately than in the past, and the number of unnecessary notifications is decreased, and the trouble of nurses or the like can be solved.

Example 3

Figure 10:
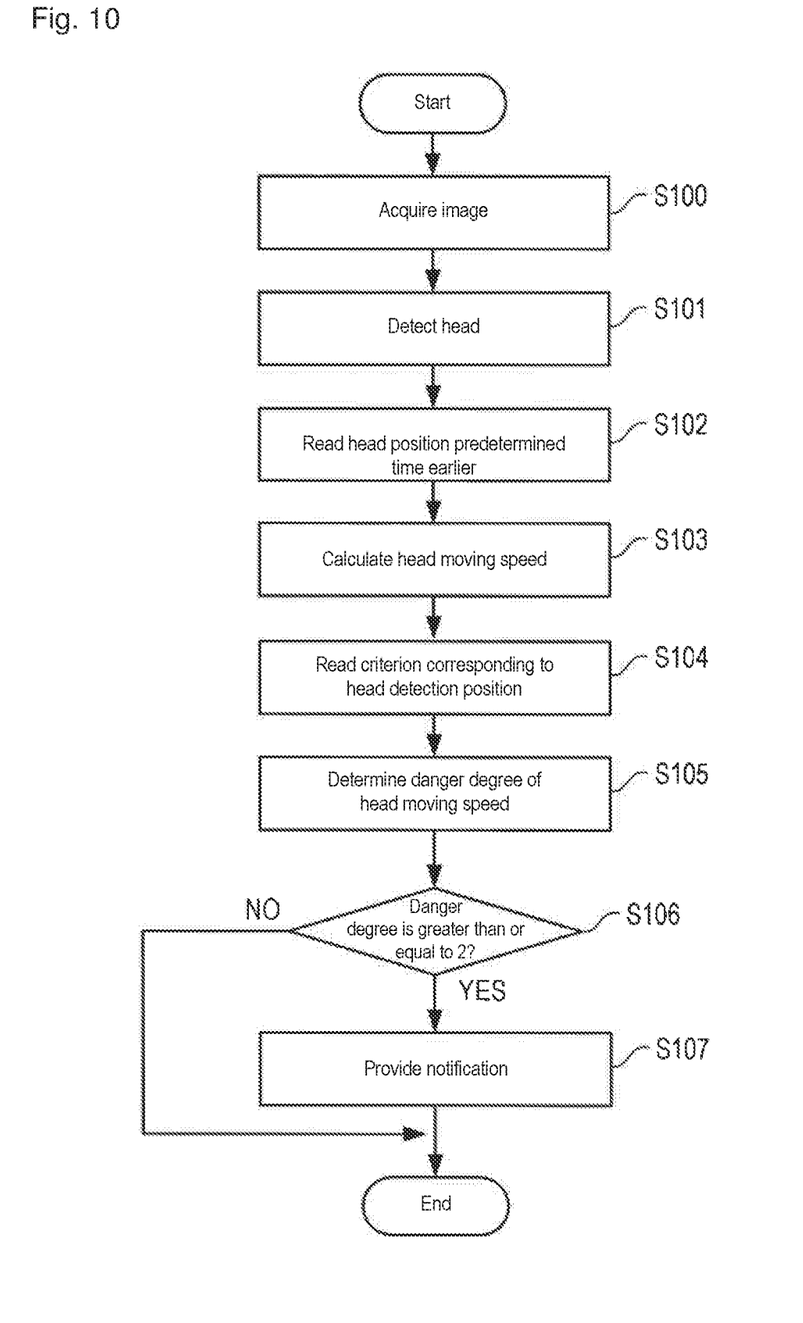
FIG. 10 is a flowchart illustrating watching processing of Example 3.

An example of the watching processing of Example 3 will be described with reference to FIG. 10. FIG. 10 is a flowchart of the watching processing of Example 3 performed by the information processing device 11.

In step S100, the image acquisition unit 110 acquires the image from the imaging device 10. The acquired image is temporarily stored in the storage 116. In step S101, the detector 111 detects the subject head from the image acquired in step S100. The information about the detected head position is stored in the storage 116 while correlated with time information or a frame number of the image. The state recognition unit 112 reads the information about the head position in the image of a predetermined time earlier (for example, one second) from the storage 116 (step S102), and the moving speed (moving amount per predetermined time) is calculated based on the head position of the predetermined time earlier and the head position detected in step S101 (step S103).

In step S104, the determination unit 113 reads the criterion corresponding to the determination region where the head is detected from the storage 116. In Example 3, the criterion in which the moving speed and the danger degree are correlated with each other is set in each determination region. For example, in the case that the head is detected in the determination region A1, the subject should be in the lying state. Thus, based on the general speed of the head (for example, 20 cm/sec) in the raising-up action (the action to raising the upper body), preferably the criterion for the determination region A1 is set (for example, danger degree=1 in the case that the moving speed is less than or equal to 20 cm/sec, danger degree=2 in the case of 20 cm/sec to 40 cm/sec, danger degree=3 in the case of being greater than 40 cm/sec, or the like). In the case that the head is detected in the determination region A3 or A4, standing-up action is assumed as action that the subject can take next. Thus, based on the general speed of the head (for example, 50 cm/sec) in the standing-up action, preferably the criterion for the determination region A3 or A4 is set (for example, danger degree=1 in the case that the moving speed is less than or equal to 50 cm/sec, danger degree=2 in the case of 50 cm/sec to 80 cm/sec, danger degree=3 in the case of being greater than 80 cm/sec, or the like).

In step S105, the determination unit 113 determines the danger degree of the moving speed of the head 22 using the criterion. The output unit 114 provides the notification according to the danger degree (step S106). In Example 3, the notification (for example, a nurse call) is provided in the case that the danger degree is greater than or equal to a predetermined threshold (for example, 2) (step S107). Similarly to Examples 1 and 2, by the method of Example 3, the danger of the subject on the bed can be detected more quickly and more accurately than in the past, and the number of unnecessary notifications is decreased, and the trouble of nurses or the like can be solved.

Example 4

Figure 11:
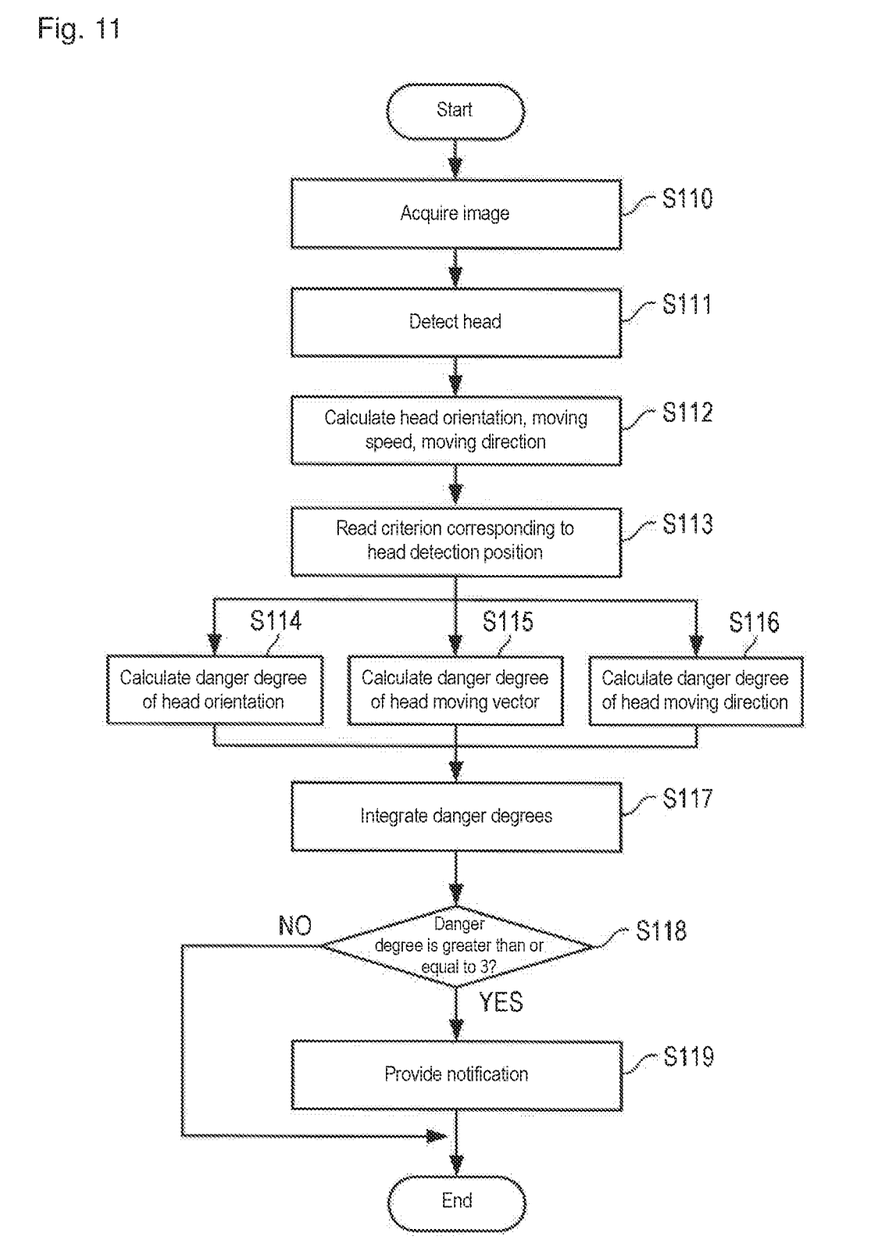
FIG. 11 is a flowchart illustrating watching processing of Example 4.

An example of the watching processing of Example 4 will be described with reference to FIG. 11. FIG. 11 is a flowchart of the watching processing of Example 4 performed by the information processing device 11.

In step S110, the image acquisition unit 110 acquires the image from the imaging device 10. The acquired image is temporarily stored in the storage 116. In step S111, the detector 111 detects the subject head from the image acquired in step S100. The information about the detected head position is stored in the storage 116 while correlated with time information or a frame number of the image. In step S112, the state recognition unit 112 calculates the head orientation, the moving speed, and the moving direction. The specific calculation method may be identical to that described in Examples 1 to 3.

In step S113, the determination unit 113 reads the criterion corresponding to the determination region where the head is detected from the storage 116. The determination unit 113 calculates the danger degree with respect to the head orientation (step S114), the danger degree with respect to the moving vector of the head (step S115), and the danger degree with respect to the moving speed of the head (step S116). The specific calculation method may be identical to that described in Examples 1 to 3. In step S117, the determination unit 113 integrates the three values of the danger degrees obtained in steps S114 to S116 to calculate an integrated score of the danger degree. For example, the maximum value among the three values may be selected as the integrated score, or the average value, the multiplication value, the addition value, or the like of three or two values may be selected as the integrated score.

In step S118, the output unit 114 provides the notification according to the integrated score of the danger degree. In Example 4, the notification (for example, a nurse call) is provided in the case that the integrated score of the danger degree is greater than or equal to a predetermined threshold (for example, 3) (step S119). Similarly to Examples 1 to 3, by the method of Example 4, the danger of the subject on the bed can be detected more quickly and more accurately than in the past, and the number of unnecessary notifications is decreased, and the trouble of nurses or the like can be solved. Additionally, the danger degree of the subject is evaluated from a plurality of points of view, so that reliability and accuracy can further be enhanced.

<Others>

The descriptions of the embodiment and Examples merely illustrate the present invention. The present invention is not limited to the above specific aspects, but various modifications can be made without departing from the scope of the technical idea thereof. For example, in Examples 1 to 4, the notification is provided only in the case that the danger degree is greater than or equal to the predetermined threshold. Alternatively, the content, the frequency, the means, and the like of the notification may be switched according to the danger degree. Information such as the determined danger degree and the notification content according to the danger degree may be output onto a screen of the information processing device 11. In this case, the information may be output in a vicinity of the subject in the image captured from the imaging device 10. The danger degree of each frame or each determination region may be averaged and output during continuous motion of the subject (lying state→raising-up state→getting-out-of-bed state).

DESCRIPTION OF SYMBOLS 1 watching assistance system
10 imaging device
11 information processing device 110 image acquisition unit
111 detector
112 state recognition unit
113 determination unit
114 output unit
115 region setting unit
116 storage
100 illumination
101 near infrared camera
20 bed
21 subject
22 head
40 to 43 four corner points of bed
44 bed region
A1 to A4 determination region

The invention claimed is:

1. A watching assistance system that assists watching over a subject on a bed, the watching assistance system comprising:
   an image acquisition unit configured to acquire an image captured by an imaging device;
   a region setting unit configured to set a plurality of determination regions;
   a criterion storage in which a criterion for determining a dangerous state is previously set for each of the plurality of determination regions set based on a region of the bed in the image;
   a detector configured to detect the subject from the image acquired by the image acquisition unit;
   a state recognition unit configured to recognize a state of a head of the subject including a head orientation of the subject detected by the detector;
   a determination unit configured to determine a danger degree of the state of the head of the subject recognized by the state recognition unit using a criterion for a determination region corresponding to a position at which the subject is detected by the detector; and
   an output unit configured to provide notification according to the danger degree determined by the determination unit.

2. The watching assistance system according to claim 1, wherein
   the state of the head includes a plurality of items including at least one of a head moving speed, a head moving direction, and a head moving vector in addition to the head orientation, and
   the determination unit determines the danger degrees relating to the plurality of items, and determines the danger degree of the state of the head by integrating the danger degrees relating to the plurality of items.

3. The watching assistance system according to claim 1, wherein the output unit does not provide notification when the determined danger degree is smaller than a threshold.

4. A method for controlling a watching assistance system that assists watching over a subject on a bed, the watching assistance system control method comprising:
   a step of acquiring an image captured by an imaging device;
   a step for setting a plurality of determination regions;
   a step of previously setting a criterion for determining a dangerous state for each of the plurality of determination regions set based on a region of the bed in the image;
   a step of detecting the subject from the acquired image;
   a step of recognizing a state of a head of the subject including a head orientation of the detected subject;
   a step of determining a danger degree of the state of the head of the recognized subject using a criterion for a determination region corresponding to the position at which the subject is detected; and
   a step of providing notification according to the determined danger degree.

5. A program causing a computer to perform each step of the watching assistance system control method according to claim 4.

6. The watching assistance system according to claim 2, wherein the output unit does not provide notification when the determined danger degree is smaller than a threshold.

7. The watching assistance system according to claim 1, wherein the criterion for each of the plurality of determination regions is defined such that the danger degree is higher when the head of the subject is oriented toward an inside of the bed than when the head of the subject is oriented toward an outside of the bed.

* * * * *